US005840668A

United States Patent [19]

Behan et al.

[11] Patent Number: 5,840,668

[45] **Date of Patent: *Nov. 24, 1998**

[54] PERFUMED LAUNDRY DETERGENT POWDERS

[75] Inventors: John Martin Behan, Kennington; Richard Arthur Birch, Hythe; John Leake, Chester; Jeremy Nicholas Ness, Canterbury; Anthony Nock, Warrington; Keith Douglas Perring, Ashford, all of Great Britain

[73] Assignee: Quest International B.V., Naarden, Netherlands

[ * ] Notice: This patent issued on a continued prosecution application filed under 37 CFR 1.53(d), and is subject to the twenty year patent term provisions of 35 U.S.C. 154(a)(2).

[21] Appl. No.: 481,483

[22] PCT Filed: Dec. 23, 1993

[86] PCT No.: PCT/EP93/03695

§ 371 Date: Nov. 14, 1995

§ 102(e) Date: Nov. 14, 1995

[87] PCT Pub. No.: WO94/16046

PCT Pub. Date: Jul. 21, 1994

[30] Foreign Application Priority Data

| | | | |
|---|---|---|---|
| Jan. 11, 1993 | [EP] | European Pat. Off. | 93300147 |
| Jan. 13, 1993 | [EP] | European Pat. Off. | 93300180 |

[51] Int. Cl.[6] .............................. A61K 7/00; C11D 3/08; C11D 3/50

[52] U.S. Cl. .......................... 510/349; 510/101; 510/102; 510/103; 510/104; 510/105; 510/106; 510/107; 510/349; 510/438; 510/441; 510/446; 510/466

[58] Field of Search .................................... 510/105–107, 510/349, 438, 441, 446, 466; 512/4

[56] References Cited

U.S. PATENT DOCUMENTS

| | | | |
|---|---|---|---|
| 4,394,127 | 7/1983 | Melville et al. | 8/137 |
| 4,954,285 | 9/1990 | Wierenga et al. | 252/174.11 |
| 4,973,422 | 11/1990 | Schmidt | 510/337 |
| 5,336,665 | 8/1994 | Garner-Grey et al. | 512/4 |
| 5,691,303 | 11/1997 | Pan et al. | 512/4 |

FOREIGN PATENT DOCUMENTS

| | | |
|---|---|---|
| 325457 | 7/1989 | European Pat. Off. . |
| 0332259 | 9/1989 | European Pat. Off. . |
| 0332260 | 9/1989 | European Pat. Off. . |
| 334490 | 9/1989 | European Pat. Off. . |
| 0425277 | 5/1991 | European Pat. Off. . |
| 478326 | 4/1992 | European Pat. Off. . |
| 2140820 | 12/1984 | United Kingdom . |

OTHER PUBLICATIONS

Chemical Abstracts, vol. 115, No. 6, Aug. 12, 1991, abstract No. 52294m, K.Mizuo "Granular Laundry detergent compositions having high bulk density and containing perfumes for fabrics", p. 148; see abstract & JP, A, 03 035 100, 15 Feb. 1991.

*Primary Examiner*—Paul Lieberman
*Assistant Examiner*—Kery A. Fries
*Attorney, Agent, or Firm*—Pillsbury Madison & Sutro LLP

[57] ABSTRACT

The invention concerns perfumed, free flowing concentrated laundry detergent powders (concentrates), having a ratio of total solid constituents to total liquid constituents of less than 30:1, wherein the perfume is sorbed onto carrier particles which release at least 60% w/w/ of the perfume in the Perfume Release Test and which are inert as defined by the Perfume Stability Test. The invention also concerns perfume-on-carrier systems designed for perfuming free flowing concentrated laundry detergent powders. Preferably the carrier particles are inorganic and have a perfume content of at least 25% w/w.

10 Claims, No Drawings

PERFUMED LAUNDRY DETERGENT POWDERS

FIELD OF THE INVENTION

The invention relates to perfumed laundry detergent powders and to perfume-on-carrier systems for incorporation into laundry detergent powders.

BACKGROUND OF THE INVENTION

Detergent powders for laundry use span a wide range of compositions. Traditional (or “regular”) products are typified by a detergent surfactant level of between 8% and 20% by weight in total, more commonly 10% to 15%. The surfactants may be anionic, non-ionic, cationic, zwitterionic or amphoteric in nature, and commercial products may contain all classes of surfactants, but the predominant form is generally anionic (i.e. anionic surfactants typically account for 50% or more of the total surfactants). Typical detergent surfactants are described in detail in “Surfactant Surface Agents and Detergents”, volume II by Schwartz, Perry and Birch, Interscience Publishers (1958). The remainder of a laundry detergent composition generally comprises builders, fillers, moisture, soil release and soil suspension and anti-redeposition agents, and other optional adjuncts such as processing aids, optical brighteners, dyes, foam control agents, anti-corrosion agents, perfumes, pH control agents, enzymes, stabilisers, bleaches and bleach activators. The level of solid components in regular laundry detergent compositions is high, usually above 75%, often above 85%. Perfume loadings for such compositions are generally within the range 0.05% to 0.4%, more commonly 0.1% to 0.3%, and the ratio of solid constituents to organic liquid constituents in a regular detergent composition is usually at least 30:1, and is likely in practice to be considerable higher, e.g. at least 150:1 and up to 500:1.

Laundry detergent powder concentrates and hyperconcentrates (for the purposes of this specification further referred to as “concentrates”) represent a relatively new product segment which is assuming increasing commercial importance world-wide. These concentrated products have a rather different composition to that described above.

The total level of detergent surfactants in concentrates generally lies within the range 15% to 60% by weight of the powder, more usually 20% to 40%. In addition to the difference in the level of surfactants another major point of difference concerns the level of low-functionality materials such as fillers. In concentrates the level of sodium sulphate for example, is rarely above 6% or even 2% by weight, whereas in regular powders levels of 20% to 30% are common. The composition of the actives may be similar to that in regular products, i.e. predominantly anionics, but not restricted to this and, for example, a high proportion of non-ionics may be used advantageously. The use of higher proportions of non-ionic surfactants is reported to be a significant trend in the detergent industry, at least for Europe, as reported by Smulders and Krings (Chemistry and Industry, March 1990, pages 160 to 163). Examples of detergent powder formulations with high non-ionics levels are disclosed in EP 228011, EP 168102, EP 425277, and EP 120492. Many non-ionic surfactants are liquid at ambient temperatures. Yet another difference between “regulars” and concentrates is that the percentage of perfume incorporated into concentrates tends to be higher than that for regular powder use, and lies generally above 0.1% by weight, normally within the range 0.4% to 2.5% by weight of the powder, more typically 0.5% to 1.5%.

Thus a concentrate may be defined for the purposes of the present specification as comprising at least 15% (and preferably at least 20%) w/w total surfactant actives and at least 0.1% w/w perfume, preferably at least 0.4% w/w. A consequence of these differences between regulars and concentrates is that the ratio of total solid to total organic liquid components for certain concentrates may be less than 30:1, or even less than 10:1, and problems can arise in manufacture and storage of the product due to “stickiness” and lump formation. In particular, for concentrates incorporating relatively high levels of liquid non-ionic surfactants, processing problems may arise from agglomeration of particles, with handling difficulties during production, and with the possibility of forming large powder conglomerates which are unacceptable to the end user of the product. Even after optimisation of the powder formulation it may be found that the addition of further liquid components such as perfumes to these systems will exacerbate the tendency for particle cohesion and agglomeration, especially when the perfume is post-dosed into base powder, and when high levels of perfume are incorporated.

The prior art literature provides many instances where perfume is delivered via the use of a solid carrier, which may be either organic or inorganic in nature, or both.

GB 2066839 discloses detergent powders containing perfume sorbed onto a porous carrier at a level of 10% to 65% by weight. The carrier is a large surface area sorbent selected from a wide variety of substrates such as polyacrylates, polyvinyl chloride, urea-formaldehyde resins, polystyrene, hydrated silicon dioxide, titanium dioxide, aluminium trioxide, or mixtures thereof. The primary objective of the invention disclosed therein is to decrease perfume losses through volatilisation and chemical attack during storage of perfumed powder products.

GB 1306924 describes perfume particles in free-flowing powder form” prepared from perfume and a particulate silica, or more particularly from a mixture of a finely divided silica and an absorbent silica gel. The fragrance loading in these particles may be as high as 70%. Manufacture is economical and involves simple mixing of perfume oil with the silicas, followed by sieving. Examples are disclosed of perfume particles suitable for use in talcum powders, scouring powders, deodorants, toilet blocks, bath crystals and foot powders. No disclosure is made of use in detergent powders, and nothing is revealed regarding perfume stability within concentrates, nor are specific physical properties such as hydrophilic character or bulk density disclosed.

U.S. Pat. No. 4209417 teaches the use of perfume particles prepared using a water-soluble polymer together with an emulsifier. The loading of perfume in these particles may be high (30% to 70%), but the manufacturing process involves drying large volumes of aqueous dispersions, with adverse consequences for throughput and economy. In addition, the perfume must be water-insoluble. The teachings of GB 2090278 are similar, except that the perfumed particle contains water but is rendered free flowing by the inclusion of excess powdered hydratable material such as anhydrous alkali metal salts. The maximum possible loading of perfume is thereby significantly reduced.

Perfume-on-carrier systems for laundry detergent compositions as disclosed in EP 334666 are designed to deliver perfume to fabric efficiently through the use of fabric substantive carriers such as selected solid nonionic or cationic surfactants. The processing involves melt blending the components followed by spray chilling, and the resulting perfume loading is likely to be low (25% w/w or less).

Similar targeted delivery of perfume is provided by the microcapsules described in EP 376385, where a complex coacervate prepared from perfume and polycationic and polyanionic materials is coated with a water-insoluble cationic fabric softener which facilitates perfume delivery to fabric. In both these inventions the cost of manufacture is relatively high and relatively complicated processing steps are involved.

GB 2140820 and GB 2141730 describe perfume-on-carrier systems based on zeolites or clays, with an optional coating of a fabric-adhesive agent, wherein the perfume loading in these carriers is low (10% or less). The carrier systems are designed to deliver perfume to fabric via the zeolite or clay, which are likely to contact fabric and be dispersed thereupon during laundering, and are hydrophobic enough to retain sufficient perfume even in the wash solution.

EP 332259 and EP 332260 detail the use of silica perfume carriers in detergent powders and fabric softeners, respectively. The silicas span a wide range of types, with particle size of from 0.001 micron (fumed silica) through to 15 micron (silica gel), with a surface area of 100–800 $m^2/g$. For laundry detergent powders the preferred silica is a fumed type, with particle size in the range 0.007 micron. to 0.025 micron, although silica gels may also be used, the preferred particle size being 1 to 8 micron. These silica carriers are optimised for application in detergent compositions providing perfume at a level of 0.01 to 0.5%, and where the perfume includes components which require protection from hostile bleaching agents present in the detergent composition. The detergent compositions contain preferably 10% to 25% of detersive surfactants. The examples given are high in anionic type surfactants, and have high solid to organic liquid ratios. It is stated in EP 332259 that "in addition to separating and protecting the perfume from the bleach, it is believed that the silica particles deposit on fabrics and enhance the delivery of the perfume to the fabrics".

SUMMARY OF THE INVENTION

It is the purpose of the present invention to provide a method for incorporating perfumes in particulate form into concentrates so as to not adversely affect the flow properties of the detergent powder by the addition of perfume. It is another purpose of the invention to provide perfume-on-carrier systems for incorporation into concentrates in which perfumes retain their integrity and which can release substantially all their fragrance to the wash liquor during conventional laundering.

DETAILED DESCRIPTION OF THE INVENTION

In one aspect the invention provides perfumed, free flowing concentrated laundry detergent powders (concentrates), having a ratio of total solid constituents to total liquid constituents of less than 30:1 and containing at least 0.1 w/w of perfume, wherein the perfume is sorbed onto carrier particles which release at least 60% w/w of the perfume in the Perfume Release Test as described herein below and which are inert as defined by the Perfume Stability Test described herein below.

In another aspect the invention provides perfume-on-carrier systems wherein the carrier particles release at least 60% w/w of the perfume in the Perfume Release Test as described herein below and are inert as defined by the Perfume Stability Test described herein below.

For the purposes of this invention a concentrated laundry detergent powder (or "concentrate") is defined as a detergent powder comprising:

at least 15% w/w, preferably at least 20% w/w, more preferably between 20 and 60% w/w of detergent surfactants (for brevity hereinafter referred to as "surfactants").

less than 10% w/w, preferably less than 6% w/w, more preferably less than 2% of fillers, such as sodium sulphate.

Furthermore concentrates preferably have a bulk-density of at least 600 g/l.

Finally, concentrates generally contain other components, such as builders (phosphates such as sodium tripolyphosphate, zeolites or NTA), soil suspension and anti-redeposition agents, enzymes, optical brighteners, processing aids, dyes, foam control agents, anti-corrosion agents, pH control agents, stabilisers. Bleaching detergents also contain bleaches and bleach activators.

The invention is particularly concerned with concentrates in which a substantial proportion, i.e. 35% w/w or more, of the surfactants is liquid at ambient temperature. In this respect it should be taken into account that in many cases a particular surfactant is in fact a mixture of chemically closely related but slightly different components, e.g. a mixture of polymers with varying degrees of polymerization. Therefore, such products do not have a sharp melting point. For the purposes of this invention a surfactant is considered liquid when at a temperature of 25° C. and above it contains no more than 50% solids.

Under this definition the vast majority of anionic, cationic, zwitterionic and amphoteric surfactants are solids and surfactants falling in the category of liquids are predominantly nonionics, although many other nonionics are solids.

The invention is therefore also particularly concerned with concentrates in which a substantial part of the surfactant is of the nonionic type. In one embodiment it is concerned with concentrates comprising mainly nonionic and anionic surfactants in which the ratio of nonionic to anionic surfactant is at least 3:2 and wherein at least 35% w/w of the total quantity of surfactants is liquid. Thus, in these concentrates generally at least 60% w/w of the nonionics is liquid. In another embodiment it is concerned with concentrates in which all of the surfactants are nonionics, of which at least 35% w/w is liquid.

The concentrates according to the invention contain the perfume-on-carrier systems according to the invention in a quantity to give at least 0.1% w/w (calculated on the total concentrate) of perfume in the concentrate, preferably 0.4–2.5% of perfume, more preferably 0.5–1.5% w/w of perfume in the concentrate. The actual quantity of perfume-on-carrier system to be added thus also depends on the perfume content in the perfume-on-carrier system as hereinbelow described.

As used herein the term "perfume" denotes a substantially water-insoluble composition of matter consisting of one or more perfume components, optionally mixed with a suitable solvent or diluent, which is used to impart a desired odour to the detergent product to which it is added and/or to the wash liquor, the skin, hair or the fabric.

Perfume components are those constituents of a perfume which are added thereto only or primarily for their olfactive contribution. Perfume components may be natural products such as extracts, essential oils, absolutes, resinoids, resins, concretes etc., but also synthetic materials such as hydrocarbons, alcohols, aldehydes, ketones, ethers, acids, esters, acetals, ketals, nitriles, etc., including saturated and unsaturated compounds, aliphatic, carbocyclic and heterocyclic compounds. Such perfume components are mentioned, for example, in S. Arctander, Perfume and Flavor Chemicals (Montclair, N.J., 1969), in S. Arctander, Perfume and Flavor Materials of Natural Origin (Elizabeth, N.J., 1960) and in "Flavor and Fragrance Materials-1991", Allured Publishing Co. Wheaton, Ill. USA.

Examples of perfume components are: geraniol, geranyl acetate, linalol, linalyl acetate, tetrahydrolinalol, citronellol, citronellyl acetate, dihydromyrcenol, dihydromyrcenyl acetate, tetrahydromyrcenol, terpineol, terpinyl acetate, nopol, nopyl acetate, 2-phenylethanol, 2-phenylethyl acetate, benzyl alcohol, benzyl acetate, benzyl salicylate, styrallyl acetate, benzyl benzoate, amyl salicylate, dimethylbenzyl carbinol, trichloromethylphenylcarbinyl acetate, p-tert-butyl cyclohexyl acetate, isononyl acetate, vetiveryl acetate, vetiverol, α-hexylcinnamaldehyde, 2-methyl-3-(p-tert-butylphenyl)propanal, 2-methyl-3-(p-isopropylphenyl) propanal, 3-(p-tert-butyl-phenyl)-propanal, tricyclodecenyl acetate, tricyclodecenyl propionate, 4-(4-hydroxy-4-methylpentyl)-3-cyclohexenecarbaldehyde, 4-(4-methyl-3-pentenyl)-3-cyclohexenecarbaldehyde, 4-acetoxy-3-pentyltetrahydropyran, 3-carboxymethyl-2-pentylcyclopentane, 2-n-heptylcyclopentanone, 3-methyl-2-pentyl-2-cyclopentenone, n-decanal, n-dodecanal, 9-decenol-1, phenoxyethyl isobutyrate, phenylacetaldehyde dimethylacetal, phenylacetaldehyde diethylacetal, geranyl nitrile, citronellyl nitrile, cedryl acetate, 3-isocamphylcyclohexanol, cedryl methyl ether, isolongifolanone, aubepine nitrile, aubepine, heliotropin, coumarin, eugenol, vanillin, diphenyl oxidet hydroxycitronellal, ionones, methylionones, isomethylionones, irones, cis-3-hexenol and esters thereof, indan musks tetralin musks isochroman musks macrocyclic ketones, macrolactone musks ethylene brassylate, aromatic nitromusks.

Suitable solvents and diluents for perfumes as mentioned above are, for example, diethyl phthalate, triethyl citrate, ethanol, isopropanol, dipropylene glycol, etc.

The perfume-on-carrier systems (hereinafter for brevity referred to as "POC systems") according to the invention comprise a perfume as defined above and an inert particulate carrier. Inertness of the carrier is tested with a test perfume as described below in the "Perfume Stability Test". For the purposes of this invention a carrier is considered inert if each component in the test perfume 1 of Table 1 below suffers no more than 5% deterioration under the test conditions.

Also the POC systems should easily release a substantial proportion of its perfume content when immersed in a laundry wash liquor. This ability requires the carrier to be sufficiently hydrophobic and the suitability of a carrier can be determined with the "Perfume Release Test" described below. For the purposes of this invention a carrier is considered to pass the test if under the test conditions it is found to release at least 60% of the test perfume 2 of Table 2 below.

The POC systems comprise preferably at least 25% w/w of perfume, more preferably at least 40% and most preferably at least 70% w/w. Yet the POC system should remain free-flowing.

Conveniently the inert carrier particles have a mean diameter in the range 5–50 microns, preferably in the range 10–50 microns, more preferably in the range 15–50 microns, most preferably in the range 20–50 microns. Also, they should preferably have a surface area in the range 100–450 $m^2/g$, more preferably in the range 100–350$m^2/g$, most preferably in the range 100–300 $m^2/g$. Preferably an inorganic carrier is used, such as a silica, zeolite or clay. Typically the carrier particles are of amorphous silica.

In addition to the POC system the concentrates according to the invention may comprise up to 20% w/w of the total perfume quantity, and preferably no more than 10%, in microencapsulated form (e.g. as spray dried starch encapsulates).

The POC systems are conveniently prepared by mixing the perfume with the carrier particles. The mixing of the perfume and the carrier may be carried out in a variety of ways known to the practitioner in the art, for example by spraying the perfume onto the particles contained in a rotary drum or positioned on a conveyor belt. A non-limiting example of a suitable procedure involves the use of a Tatham-Forberg mixer in a low speed, short duration operation. The equipment comprises a twin-drum assembly with a rotary twin-shaft arrangement. Attached to each shaft is a set of carefully profiled paddles positioned at specific angles. The powder charge is fluidised by the paddle rotation and the perfume oil is sprayed on and mixing is continued until perfume take up is complete. The perfumed particle mass is then dropped through the bottom of the mixer into a suitable container.

Absorption or adsorption of perfumes into or onto inert carrier particles will not necessarily protect the perfumes against attack by bleaching compounds. Thus, for use in concentrate formulations containing bleaching agents (which are particularly hostile to perfume components) the perfume is preferably one which is resistant to such attack and retains high performance even when stored in the presence of such hostile ingredients. Suitable non-limiting examples are disclosed in EP 299561 and U.S. Pat. No. 4663068.

The POC systems of the present invention may be incorporated into concentrates using standard powder handling equipment, known in the art, e.g. by utilisation of weighbelts.

CONCENTRATE FORMULATION EXAMPLES

High non-ionic surfactant content concentrates within the scope of application defined herein are detailed in the references cited above, and two examples are shown below in Tables I and II.

TABLE I

| CONCENTRATE "A" | % w/w |
|---|---|
| Zeolite 4A | 33.2 |
| Sodium carbonate | 11.2 |
| Dobanol 23-3 | 12.1 |
| Dobanol 23-6.5 | 10.2 |
| Sodium LAS | 6.2 |
| Sodium sulphate | 3.8 |
| Polyacrylate (mw 3000–4000) | 3.5 |
| Sodium silicate | 1.9 |
| Sodium soap | 2.6 |
| POC system particles | 2.0 |
| Enzymes | 1.3 |
| Anti-redeposition agent | 0.9 |
| Antifoam | 0.4 |
| Sodium EDTA | 0.4 |
| Water, dye, minor components | 10.3 |
| | 100 |

TABLE II

| CONCENTRATE "B" | % w/w |
|---|---|
| Zeolite 4A | 29.8 |
| Sodium perborate* | 15.6 |
| Sodium carbonate | 9.7 |

TABLE II-continued

| CONCENTRATE "B" | % w/w |
|---|---|
| TAED granules** | 8.2 |
| Dobanol 23-3 | 8.7 |
| Dobanol 23-6.5 | 7.3 |
| Sodium LAS | 5.1 |
| Polyacrylate (mw 3000–4000) | 3.1 |
| Sodium sulphate | 1.6 |
| POC system particles | 1.2 |
| Sodium soap | 1.5 |
| Sodium silicate | 1.5 |
| Enzymes | 0.8 |
| Anti-redeposition agent | 0.4 |
| Sodium EDTA | 0.3 |
| Antifoam | 0.3 |
| Water, dye, minor components | 4.9 |
| | 100 |

*monohydrate
**tetraacetalythylene diamine sodium salt

Perfume Stability Test

A particulate sample (2 g) was prepared by incorporating 20% of the perfume test mixture 1 detailed in Table 1 into an inorganic carrier under evaluation. The sample was stored in glass vials (10 ml) for one week at 37° C. prior to analysis. The vials were tightly sealed and free movement of air throughout the test system was minimised by packing the free headspace volume with cotton wool.

Analysis was carried out by extraction of the sample using ethyl acetate, followed by determination of the residual mass of the indicator materials using standard gas chromatographic techniques.

Suitable carriers according to this test are those for which each of the indicator materials suffer no more than 5% degradation (i.e. each component in the system displays at least 95% stability). Such carriers are defined as passing the Perfume Stability Test for the purposes of the present application.

TABLE 1

Perfume Test Mixture 1

| Material | w/w % |
|---|---|
| Benzyl acetate | 25 |
| Limonene | 25 |
| Tetrahydrolinalol | 25 |
| Inert internal standard* | 25 |

*e.g. Tetradecane

Perfume Loading

Equal amounts of carrier material were placed in a series of glass vials and various aliquots of a mixture of perfume components were added (Perfume Test Mixture 2 as shown in Table 2). Each carrier/perfume system was agitated with a spatula, sealed in the vial and stored at ambient temperature for 24 hours prior to inspection. "Perfume Loading" was taken as the loading at which the perfume-on-carrier mixture ceased to flow easily as judged by eye.

TABLE 2

Perfume Test Mixture 2

| Material | w/w % |
|---|---|
| Benzyl acetate | 20 |
| Hexylcinnamic aldehyde | 20 |
| PTBCHA | 20 |
| Tetrahydrolinalol | 20 |
| Tonalid | 20 |

KEY: "Tonalid" is a trademark for 1,1,2,4,4,7-hexamethyl-6-acetyl-1,2,3,4-tetrahydronaphthalene
"PTBCHA" is 4-tert.butylcyclohexyl acetate Perfume Release Test The POC system under evaluation (containing at least 20% by weight of Perfume Test Mixture 2, Table 2) were equilibrated for 3 days and then added at ambient temperature to an aqueous model wash liquor at a level yielding a theoretical maximum perfume concentration of 40 ppm. The wash liquor (10 g) comprised ca. 0.05% of a mixture of a non-ionic surfactant (Dobanol 25™, a mixture of ethoxylated fatty alcohols with an average of 7 ethoxyl groups) and an anionic surfactant (sodium lauryl sulphate) in a weight ratio of 2.3 to 1.

The mixture was shaken for 10 seconds and immediately placed in a centrifuge and spun for 5 minutes at 2000 RPM.

The bulk of the supernatant liquid was withdrawn (ca. 95% by weight of the aqueous phase, measured accurately) and filtered prior to extraction with ethyl acetate (10 g, containing hexadecane as an internal standard). The ethyl acetate was obtained by centrifugation and was analysed by gas chromatography. The amount of perfume released into the aqueous phase was then calculated.

A perfume release efficiency of 60% or over is taken as indicative of bulk release of the perfume under actual wash conditions where temperatures of 35° C. to 65° C. or higher are common, and longer wash times are likely (e.g. 15–30 minutes, or longer in a soak regime). Carrier materials achieving this are considered to pass the Perfume Release Test.

Carrier material test examples

A range of commercial inorganic particles was subjected to the above tests. The results of these tests together with other relevant data are shown in Tables 3 and 4. It can be seen that the two precipitated silicas meet the criteria specified above, Neosyl GP™ and HP 39™.

TABLE 3

| | Surface Area | Mean Particle Size | Perfume Loading | Stability | | |
|---|---|---|---|---|---|---|
| Carrier | $m^2/g$ | micron | % w/w | BA | Lim | THL |
| Gasil 200* | 750 | 4.6 | 20 | 95 | 90 | 100 |
| Neosyl GP* | 200 | 18 | 65 | 95 | 95 | 95 |
| Aerosil 200** | 200 | 0.01 | 80 | 100 | 90 | 100 |
| Zeolite 4A* | — | — | 30 | 85 | 85 | 100 |
| Gasil EBN* | 320 | 9 | 55 | 100 | 85 | 100 |

TABLE 3-continued

| Carrier | Surface Area m$^2$/g | Mean Particle Size micron | Perfume Loading % w/w | Stability BA | Lim | THL |
|---|---|---|---|---|---|---|
| HP39* | 300 | 11 | 65 | 95 | 95 | 95 |
| Aerosil 300** | 300 | 0.01 | 75 | 95 | 90 | 100 |
| Neosyl LD* | >400 | 12 | 25 | 90 | 95 | 100 |

Key: BA-Benzyl acetate Lim-Limonene THL-tetrahydrolinalol (i.e. the perfume components of Perfume Test Mixture 1)

TABLE 4

Perfume Release

| Carrier | % Perfume released |
|---|---|
| Aerosil 200** | 52 |
| Aerosil R812** | 42 |
| Gasil 200** | 20 |
| HP39* | 70 |
| Neosyl GP* | 68 |

Key: */** as for Table 4

Application Example 1

POC system particles containing 50% perfume were prepared from Neosyl Gp™ and fragrance "A" as specified in Table 5. These were incorporated into concentrate powder (formulation A, Table 1) at a level of 1.1% to yield a perfume loading of 0.55%. The powder was stored in domestic laminated cardboard containers at 37° C./70% RH (relative humidity) for 4 weeks and examined. No adverse effect was noted on powder flow properties.

Application Example 2

POC system particles containing 50% perfume were prepared from Neosyl GP™ and fragrance "A" as specified in Table 5. These were incorporated into a concentrate powder (formulation B, Table 1) at a level of 1.1% to yield a perfume loading of 0.55%. The powder was stored in domestic laminated carboard containers at 37° C./70% RH (relative humidity) for 4 weeks and examined. No adverse effect was noted on powder flow properties.

Application Example 3

POC system particles containing 55% perfume were prepared were prepared from Neosyl GP™ and fragrance "B" as specified in Table 6. These were incorporated into a concentrate powder (formulation B, Table 1) at a level of 1.45% to yield a perfume loading of 0.8%. The powder was stored in domestic laminated cardboard containers at 37° C./70% RH for 4 weeks and examined. No adverse effects was noted on powder flow properties.

Application Example 4

POC system particles containing 55% perfume were prepared from HP 39™ and fragrance "B" as specified in Table 6. These were incorporated into a concentrate powder (formulation B, Table 1) at a level of 1.4% to yield a perfume loading of 0.8%. The powder was stored in domestic laminated carboard containers at 37° C./70% RH for 4 weeks and examined. No adverse effect was noted on powder flow properties.

Application Example 5

A starch encapsulate was prepared containing 40% perfume oil. The starch was a modified waxy maize starch (Capsul™, National Starch) and the perfume was a freshness accord (Fragrance C, Table 7) of perfume materials susceptible to attack by bleach components in laundry powder. The encapsulate was prepared by normal spray-drying procedures, well known to those experience in the art. An emulsion of 40% starch in water was prepared and sufficient perfume added to constitute 40% of the total of starch and perfume. This emulsion was then spray-dried using a conventional spray-dryer (Niro Mobile Minor) with rotary atomizer, inlet temperature 240° C., outlet temperature 100° C.

POC system particles containing 50% perfume were prepared from Neosyl GP™ and fragrance "B" (see Table 6). These were mixed into a concentrate powder (formulation B, Table 1) at a level of 1.1% to yield a perfume loading of 0.55%. To this product was then mixed in 0.2% of the starch encapsulate detailed above, yielding an overall perfume level of 0.63%. The powder was stored in domestic laminated cardboard containers at 37° C./70% RH for 4 weeks and examined. No adverse effect was noted on powder flow properties.

TABLE 5

Formulation of fragrance "A"

| Material | Quantity % |
|---|---|
| Anther (Q) | 1.0 |
| Coumarin | 2.0 |
| Gyrane (Q) | 0,5 |
| Hexyl cinnamic aldehyde | 18.0 |
| Jasmacyclene (Q) | 5.0 |
| Jasmopyrane Forte (Q) | 4.0 |
| Lilial (G) | 10.0 |
| Lixetone (Q) | 8.0 |
| Methyl ionone alpha iso (Q) | 5.0 |
| 4-tert.butylcyclohexyl acetate (Q) | 5.0 |
| 2-Phenylethyl alcohol | 15.0 |
| Pivacyclene (Q) | 0.5 |
| Tetrahydrolinalol | 6.0 |
| Traseolide (Q) | 20.0 |

Q: trade mark material available from Quest
G: trade mark material available from Givaudan

TABLE 6

Formulation of fragrance "B"

| Material | Quantity % |
|---|---|
| Dimethylbenzyl carbinyl acetate | 15.0 |
| 4-tert.butylcyclohexyl acetate (Q) | 17.5 |
| Tetrahydrolinalol | 15.0 |
| Anther (Q) | 3.5 |
| Traseolide (Q) | 5.0 |
| Decanol | 5.0 |
| Phenylpropanol | 6.0 |
| Herboxane | 10.0 |
| Diphenylmethane | 5.0 |
| Cedramber (IFF) | 4.0 |
| Hexadecanolide | 5.0 |
| 2-Phenylethyl alcohol | 6.0 |
| Dihydroterpineol | 3.0 |

Q: trade mark material available from Quest
IFF: trade mark material available from IFF

TABLE 7

| Formulation of fragrance "C" | |
|---|---|
| Material | Quantity % |
| Adoxal (G) | 1.0 |
| Aldehyde C9 50% in DEP | 7.0 |
| Aldehyde C10 50% in DEP | 16.0 |
| Aldehyde C11 (undecylenic) 50% in DEP | 30.0 |
| Aldehyde C12 50% in DEP | 10.0 |
| Methyl nonyl acetaldehyde 50% in DEP | 36.0 |

G: trade mark material supplied by Givaudan
DEP: diethylphthalate (diluent)

We claim:

1. A perfumed, free flowing concentrated laundry detergent power comprising:

at least 15% w/w of detergent surfactants, less than 10% w/w of fillers, having a ratio of total solid constituents to total liquid constituents of less than 30:1 and containing at least 0.1% w/w of perfume, wherein the perfume is added as a perfume-on-carrier system consisting of amorphous silica having a mean diameter in the range of 20–50 microns which further have a surface area in the range of 100–450 $m^2$/gram which carry at least 25% w/w of perfume, which release at least 60% w/w of the perfume in a Perfume Release Test and which are inert as defined by a Perfume Stability Test.

2. A detergent powder according to claim 1, having a bulk density of at least 600 g/l.

3. A detergent powder according to claim 1 or 2 wherein the amount of detergent surfactant is at least 20% w/w and the amount of filler is less than 6% w/w.

4. A detergent powder according to claim 1, wherein at least 35% w/w of the surfactants are liquids.

5. A detergent powder according to claim 4 comprising nonionic and anionic detergent surfactants wherein the ratio of nonionic detergent surfactants to anionic detergent surfactants is at least 3:2 and at least 60% w/w of the nonionic detergent surfactants is liquid.

6. A detergent powder according to claim 4 wherein all detergent surfactants are nonionic of which at least 35% are liquid.

7. A detergent powder according to claim 1 wherein the carrier particles carry at least 40% w/w of perfume.

8. A detergent powder according to claim 7, wherein the carrier particles have a surface area in the range 100–350 $m^2$/gram.

9. A perfume-on carrier system consisting of amorphous having a mean diameter in the range of 20–50 microns which further have a surface area in the range of 100–450 $m^2$/gram and which carry at least 25% w/w of perfume, which release at least 60% w/w of the perfume in a Perfume Release Test and which are inert as defined by a Perfume Stability Test.

10. A perfume-on-carrier system according to claim 1, wherein the carrier particles have a surface area in the range 100–350 $m^2$/gram.

* * * * *